United States Patent [19]
George et al.

[11] Patent Number: 6,165,449
[45] Date of Patent: Dec. 26, 2000

[54] METHODS AND COMPOSITIONS FOR IMPROVING SUN PROTECTION FROM SUNSCREEN FORMULATIONS

[75] Inventors: Liliana George, Wilmette, Ill.; John Sottery, Milford, Conn.

[73] Assignee: Stepan Company, Northfield, Ill.

[21] Appl. No.: 08/587,236

[22] Filed: Jan. 16, 1996

[51] Int. Cl.⁷ .............................. A61K 7/42; A61K 7/44; A61K 7/00
[52] U.S. Cl. .............................. 424/59; 424/60; 424/400; 424/401
[58] Field of Search ................................ 424/59, 60, 400, 424/401

[56] References Cited

U.S. PATENT DOCUMENTS 4,333,920  6/1982  Conner .

FOREIGN PATENT DOCUMENTS 0 220 934  5/1987  European Pat. Off. .
2 370 469  6/1978  France .
2 574 399  6/1986  France .
1 492437  1/1970  Germany .

*Primary Examiner*—Shelley A. Dodson
*Attorney, Agent, or Firm*—McDonnell Boehnen Hulbert & Berghoff

[57] ABSTRACT

Disclosed are methods and compositions for increasing the sun protection factor of oil and water sunscreen emulsions comprising adding a phthalic acid derivative to an oil and water sunscreen emulsion in an amount effective to increase the sun protection factor of the emulsion, the phthalic acid derivative having the general formula:

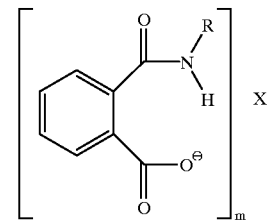

where

R represents an organic substituent, X represents a cation; and m is an integer satisfying the valency of X.

20 Claims, No Drawings

METHODS AND COMPOSITIONS FOR IMPROVING SUN PROTECTION FROM SUNSCREEN FORMULATIONS

BACKGROUND OF THE INVENTION

1. Field of the Invention

This invention relates to skin-care products in general and specifically to sunscreen formulations comprising an emulsion of water and at least one oil. In particular, it relates to oil and water emulsions containing organic sunscreens or containing organic and/or inorganic (physical) sunscreen components. It further relates to suncare/skincare compositions capable of providing a high degree of protection from the harmful effects of ultraviolet radiation, such as sunburn and sun-induced premature aging.

2. Description of the Related Art

Ultraviolet radiation (UVR) is defined as radiation beyond the visible portion of the electromagnetic spectrum at its violet end. UVR consists of wavelengths from 200 to 400 nm and is subdivided into three bands from longer to shorter wavelengths as ultraviolet A (UVA), ultraviolet B (UVB), and ultraviolet C (UVC), respectively.

Human skin has a limited capacity to adapt to certain UV radiation when exposure to solar radiation is increased gradually. However, this protective mechanism fails when exposure increases abruptly. The sunburn response is generally associated with UVB exposure. Recent work, however has shown that large doses of UVA have detrimental effects on skin as well.

The damaging effects of sunlight on skin are well documented. The combination of a diminished ozone layer with the growing tendency for people to engage in outdoor activities is believed to increase the occurrence of skin cancer and also to accelerate premature aging of the skin.

As the body of evidence regarding the harmful effects of UV radiation grows, the cosmetic industry continues to formulate new products for providing enhanced protection against UVB and UVA radiation. Sunscreen agents or sunfilters are now incorporated into a variety of products for everyday use. These include moisturizers, creams, lotions, foundations, lipsticks, and other miscellaneous skin care products as well as shampoos and mousses. Such formulations are designed to at least partially protect human skin and hair from UV radiation.

The protective strength of a particular sunscreen agent on the skin depends on a variety of factors. Among these factors are distribution (or deployment) of the sunscreen molecules on the skin, the spectral UV properties of the sunscreen, the photostability of the sunscreen, the chemical structure, the concentration of the sunscreen, the penetration of the sunscreens into the stratum corneum, and the spreading properties of the vehicle and the subsequent adherence to skin.

Deployment of the sunscreen molecules over the surface of the skin determines to a major extent the protection delivered by various sunscreen formulations. Sunscreen formulations should be designed such that when applied to skin they deliver a film that covers both the peaks and the valleys of skin. Ideally, the sunscreen formulation can be applied to yield a film of uniform thickness on the skin with the sunscreen molecules homogeneously distributed within the film. The vehicle (the non-sunscreen component of the formulation) determines the manner in which the sunscreen molecules are deployed on the skin. In addition, the vehicle also controls to a large extent the ability of a sunscreen to protect skin after prolonged water exposure. Beyond protecting the skin from UV radiation, other formulation attributes such as product mildness and cosmetic elegance are also important to consumers.

The most common formulation type for topical sunscreens is an emulsion. Sunscreen products may be manufactured as either oil-in-water (O/W) or water-in-oil (W/O) emulsions. Consequently, it is important that the emulsification system be capable of creating stable emulsions with a variety of polar and non-polar sunscreen agents as well as cosmetic oils.

SUMMARY OF THE INVENTION

Cosmetic chemists have devoted much effort towards developing methods and compositions for improving the SPF ("sun protection factor") efficiency of sunscreen vehicles, i.e. delivering higher sun protection factor with a given amount of sunscreening agent. The present invention provides novel methods and compositions for unexpectedly improving the sun protection factor of formulations employing in some embodiments, relatively low levels of various organic and/or inorganic (physical) sunscreen components.

More specifically, the invention provides methods and compositions for increasing the sun protection factor of an oil and water sunscreen emulsion. The invention comprises adding a phthalic acid derivative to an oil and water sunscreen emulsion in an amount effective to increase the sun protection factor of the emulsion. The emulsions of the invention may be oil-in-water or water-in-oil emulsions. Such emulsions are typically prepared by preparing and combining water and oil phases to produce an emulsion.

The phthalic acid derivatives useful in the invention are encompassed by the general structure shown below in Formula I:

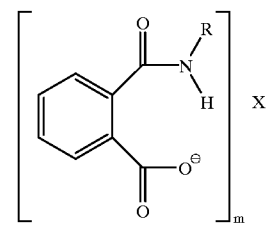

wherein

R represents $C_8$–$C_{40}$ alkyl, $C_8$–$C_{40}$ alkenyl, alkylaryl where the alkyl portion is $C_8$–$C_{40}$ alkyl, aryl, $C_3$–$C_7$ cycloalkyl, or $R_1$—O—$R_2$ where $R_1$ and $R_2$ independently represent $C_1$–$C_{22}$ alkyl, $C_1$–$C_{22}$ alkenyl, alkylaryl where the alkyl portion is $C_1$–$C_{22}$ alkyl, aryl, or $C_3$–$C_7$ cycloalkyl;

X represents a cation; and m is an integer satisfying the valency of X.

The emulsions of the invention may be prepared by adding the phthalic acid derivative to either the water phase or the oil phase prior to preparing the emulsion.

The compositions of the invention provide important advantages. Among these advantages are increased sun protection factor efficiency, increased mildness to human skin and scalp, and an absence of soaping and minimal whitening when applied to the skin. Further, the inventive compositions are easy to spread, adhere well to the skin, and are waterproof.

As can be seen in the examples, the compositions of the present invention yield higher sun protection factors (SPFs)

than do compositions without the phthalic acid derivative but having the same amount of active sunscreen agents. Consequently, sunscreen formulations prepared according to the invention require less of an active sunscreen agent to achieve SPFs similar to conventional sunscreen formulations. In addition, since the active sunscreen agent contributes a major portion of the cost of the final formulation, significant cost savings can be realized with this invention. Further, because high levels of organic sunscreens can irritate skin of certain individuals, formulations of the invention are generally more mild than conventional formulations having similar SPFs, due to the decreased concentration of organic sunscreens and the inherent mildness of the emulsification system.

DETAILED DESCRIPTION OF THE INVENTION

Sunscreen compositions according to the invention comprise an oil and water emulsion. Such oil and water emulsions comprise oil components, water, and, optionally, water soluble components. These inventive compositions further comprise at least one sunscreen compound and a sun protection factor enhancement system. Preferred compositions comprise a combination of sunscreen components. The sun protection factor enhancement system includes a low hydrophilic/lipophilic balance (HLB) emulsifier and a phthalic acid derivative of Formula I above.

The oil components include the sunscreen agents, the sunscreen enhancing system, various cosmetic oils and other oil soluble ingredients (e.g. polymers, waxes). The phthalic acid derivative may be incorporated into the emulsion either by way of the oil phase of the emulsion or alternatively by way of the water phase of the emulsion.

The oil component forming the vehicle may comprise one or more hydrophobic materials. These materials are hydrophobic oils that are insoluble in water. Representative oils suitable for use in the inventive compositions include, but are not limited to isopropyl palmitate (IPP), octyl isononanoate (OIN), octyl dodecyl neopentanoate (e.g. Elefac I-205), isohexadecane (e.g. Permethyl 101A), hydrogenated vegetable oil (e.g. Vegepure). Other suitable oils include mineral oil, petrolatum, isopropyl myristate, triglycerides, and various silicones including dimethicones and cyclomethicones, etc.

The sun protection factor enhancement system typically includes a low HLB emulsifier such as glycerol esters including glycerol monostearate (GMS) and glycerol monooleate (GMO), ethylene glycol distearate (EGDS), PEG esters such as polyethylene glycol monostearate, polyglyceryl esters such as polyglyceryl-10-decaoleate (e.g.Drewpol), and silicone emulsifiers such as polysiloxane based water-in-oil emulsifiers (e.g. Abil EM-90). These low HLB emulsifiers have HLB's of from about 1 to 6, and preferably from about 1.5 to about 3.8.

As noted above, the sun protection factor enhancement system also includes a phthalic acid derivative of formula I that may be added with the oils or with the water. The phthalic acid derivative is present in the final sunscreen emulsions in an amount of about 0.1 to about 15% by weight of the emulsion. Preferred sunscreen emulsions of the invention comprise about 0.5 to 10% of the phthalic acid derivative by weight of the emulsion. Most preferred sunscreen emulsions of the invention comprise about 1 to 5% of the phthalic acid derivative by weight of the emulsion.

Preferred compounds of Formula I are those where R represents straight or branched chain alkyl groups having from about 8–22 carbon atoms; m is 1; and X is sodium, potassium, ammonium, mono-, di-, or trialkanolamonium, more preferably ethanolammonium, mono-, di-, or trialkylammonium, more preferably ethanolammonium. Yet more preferred compounds of Formula I are those where R represents straight or branched chain alkyl having from about 12–20 carbons atoms; m is 1; and X is sodium, potassium, or triethanolammonium.

Representative cations, i.e., "X" groups, include $Mg^{++}$, $Ca^{++}$, $Na^+$, $K^+$, $NH_4+$, and $R_1R_2R_3NH^+$, where $R_1$, $R_2$, and $R_3$ independently represent $C_{1-6}$ straight or branched chain alkyl groups or $C_{1-6}$ straight or branched chain alkylol groups.

Representative phthalic acid derivatives of formula I suitable for use in the sunscreen compositions include, for example, sodium soyaamido benzoate, sodium oleylamido benzoate, potassium cocoamido benzoate, and sodium stearylamido benzoate. Suitable phthalic acid derivatives are commercially available from Stepan Company, Northfield, Ill.

The level of oil components in the emulsion is generally from about 1 to 65% by weight of the emulsion. More preferred formulations of the invention comprise about 5–40% by weight of the oil components. Most preferred formulations of the invention comprise about 10–30% by weight of the oil components.

The sunscreen component for use in the inventive compositions may be a single sunscreen or a mixture of more than one sunscreen. The sunscreens may be organic or inorganic sunscreens, or a combination of organic and inorganic sunscreens. Suitable sunscreens are those capable of blocking, scattering, absorbing or reflecting UV radiation. Inorganic sunscreens, often referred to as physical sunscreens, typically scatter, reflect and absorb UV radiation while organic sunscreens generally absorb UV radiation. Representative sunscreen components capable of protecting human skin from the harmful effects of UV-A and UV-B radiation are set forth below in table 1.

TABLE 1

| CTFA Name | FDA Name/Chemical name |
|---|---|
| Benzophenone-3 | Oxybenzone/2-Hydroxy-4-methoxy benzophenone |
| Octylmethoxycinnamate | 2-Ethylhexyl-p-methoxy cinnamate |
| Benzophenone-4 | Sulisobenzone/2-Hydroxy-4-methoxy benzophenone-5-sulfonic acid |
| Octylsalicylate | 2-Ethylhexyl salicylate |
| Triethanolamine salicylate | Triethanolamine o-hydroxybenzoate |
| Glyceryl PABA | Glyceryl p-aminobenzoate |
| Padimate O | Octyldimethyl p-aminobenzoate |
| Homosalate | Homomenthyl salicylate |
| PABA | p-Aminobenzoic acid |
| Padimate A | Amyldimethyl PABA |
| Benzophenone-8 | Dioxybenzone |
| Octocrylene | 2-Ethyl-hexyl-2-cyano-3,3-diphenylacrylate |
| Phenyl Benzimidazole sulfonic acid | 2-Phenylbenzimidazole-5-sulfonic acid |
| Titanium dioxide | Titanium dioxide |
| Melanin coated titanium dioxide | |
| Zinc oxide | Zinc oxide |
| Avobenzone | Butyldibenzomethane |

Preferred sunscreens and sunscreen combinations are ethyl hexyl-p-methoxy-cinnamate (commerically available from Givaudan as Parsol MCX), Benzophenone-3

(Oxybenzone commercially available from Haarmann & Reimer), 2-phenylbenzimidazole-5-sulfonic acid (commercially available as Eusolex 232 from Rona), and octyldimethyl p-amino benzoic acid (octyl dimethyl PABA commercially available from Haarmann & Reimer).

Preferred inorganic (physical) sunscreens include appropriately sized particles of micronized titanium dioxide ($TiO_2$) and zinc oxide (ZnO). In addition, these particles may have various surface treatments to render the surface non-reactive and/or hydrophobic. Inorganic sunscreens may be added to the inventive formulations on a dry basis or as predispersed slurries.

In the case of predispersed slurries, well dispersed sluries are prefered. Representative non-limiting examples of currently preferred inorganic sunscreens include a slurry of 40% by weight of aluminum stearate coated micronized titanium dioxide in Octyl dodecylneopentanoate (commercially available as TiOSperse I from Collaborative Laboratories); a slurry containing 40% by weight of a mixture of $TiO_2$ and aluminum stearate in caprylic/capric triglyceride (commercially available as TiOSperse GT from Collaborative Laboratories); a 40% slurry of glycerol coated $TiO_2$ in butylene glycol and glycerin (commercially available as TiOSperse BUG/Gly from Collaborative Laboratories); melanin coated $TiO_2$ (commercially available from MelCo); ultrafine silicone coated $TiO_2$ (commercially available as UV-Titan from Presperse, Inc.); Dimethicone coated ZnO (commercially available as Z-cote HP1 from SunSmart, Inc.); a 60% $Tio_2$, aluminum stearate, an trifluoromethyl-$C_{1-4}$ alkyldimethicone in octyl dodecylneopentanoate (commercially available as ON60TA from Kobo Products, Inc.); and a 40% $TiO_2$ slurry in octyl palmitate (commercially available as Tioveil OP from Tioxide Specialties, Ltd.).

The sunscreen emulsions are typically prepared by combining water and aqueous components (the "water phase") with any oil components (the "oil phase") where each of the phases have been optionally heated to about 70–80° C., preferably heating the resulting mixture, and subsequently mixing, preferably at an elevated temperature such as, for example, about 70–80° C., to prepare the emulsion. After cooling, a preservative may optionally be added and the pH adjusted as necessary, with, for example, citric acid.

The oil phase used to prepare the emulsion includes the low HLB emulsifier, various oils, and the sunscreen component(s). The phthalic acid derivative may be present in the water phase, the oil phase, or in both, prior to combining the phases to prepare the emulsion.

The pH of the resulting sunscreen formulations is normally between about 6 and 9, preferably between about 7 and 8, and most preferably between about 7.5 and 8.

All documents, e.g., patents and journal articles, cited above or below are hereby incorporated by reference in their entirety.

In the following examples, all amounts are stated in percent by weight of active material unless indicated otherwise.

One skilled in the art will recognize that modifications may be made in the present invention without deviating from the spirit or scope of the invention. The invention is illustrated further by the following examples which are not to be construed as limiting the invention or scope of the specific procedures or compositions described herein.

In Vitro Determination of Sun Protection Factor (SPF) of Sunscreen Formulations

The following method for determining SPF for the formulations of the invention employs a synthetic substrate (Vitro-Skin™) that mimics the surface properties of human skin.

1. A series of 6 cm by 9 cm pieces of Vitro-Skin™ are placed in a humidity controlled chamber for about 16 hours. The humidity control chamber contains a solution of about 70% water and 30% glycerin and is maintained at 23° C.

2. 100 μl of the sunscreen formulation to be tested is drawn into a calibrated positive-displacement pipette.

3. A 6 cm×9 cm piece of Vitro-Skin™ substrate is removed from the hydration chamber and placed on a plastic-covered foam block such that the skin topography side (the dull or non-shiny side) is away from the foam block. The 100 μl of sample sunscreen formulation is pipetted evenly across a 6×8 cm section of the substrate by dotting it approximately at 30 equally spaced points across the substrate.

4. The sample sunscreen formulation is then rubbed into the substrate and with sufficient force to slightly deform the plastic covered flexible foam. The product is then allowed to dry for 15 minutes after which the substrate is trimmed and then mounted on a 6 cm×6 cm slide. A second piece of substrate (untreated) is removed from the hydration chamber and mounted on a separate 35 mm slide mount to be used as a control.

5. Sun protection factors are then determined using an Optometrics SPF-290 instrument. The control (untreated piece of substrate) is then placed above the integrating sphere of the instrument and a reference scan is obtained by recording the photocurrent at 5 nm increments between 290 and 400 nm. The in vitro sun protection factor for each formulation according to the invention is then determined by placing the product treated substrate above the integrating sphere. The sample scan is then obtained by recording the photocurrent at 5 nm increments between 290 and 400 nm. Monocromatic Protection Factors (MPF) are subsequently calculated by taking the ratio of the photocurrent untreated vs. treated at each wavelength.

In Vivo Determination of Waterproof Sun Protection Factor (SPF) of Sunscreen Formulations The following method is used to determining the in vivo waterproof SPF for the formulations of the invention. The method employs a 150 watt xenon arc solar simulator commercially available as Model 12S, 14S, or 600 from Solar Light Co., Philadelphia, Pa., as a source of ultraviolet radiation. These models have a continuous emission spectrum in the UV-B range from 290–320 nm.

UV radiation is continuously monitored during a period of exposure using a Model DCS-1 Sunburn UV Meter/Dose Controller System (available from Solar Light Co.). Measurements are taken at a position within 8 mm of the skin surface. The field of irradiation is 1 cm in diameter.

The procedure for this study is essentially as described in the Federal Register, 43: 38264–38267 (1978).

A single test site area is used to determine a subjects minimal erythema dose (MED). This is accomplished by exposing the subject back to a series of timed incremental UV exposures at 25% intervals. An individual subject's MED is the shortest time of exposures that produces minimally perceptible erythema at 16 to 24 hours post irradiation. The test area is defined as the infrascapular area of the back to the right and left of the midline. A 8% homosalate standard is delivered to the test site through plastic volumetric syringe. The homosalate standard is evenly applied to a rectangular area measuring about 5 cm×10 cm for a final concentration of 2.0 mg/$cm^2$.

Fifteen minutes after the application of the homosalate standard, a series of UV light exposures in 25% increments calculated from previously determined MED's bracketing the intended SPF were administered from the solar simulator to subsites within the treated area. On the actual day of testing another series of exposures similar to the one given on the previous day was administered to an adjacent untreated site of unprotected skin to re-determine the MED. An adjacent test site was then selected for a static determination of the test substance, conducted as above, prior to the immersion test.

WATERPROOF DETERMINATION

The following determination indicates the substantivity of a sun protection emulsion and its ability to resist water immersion.

On the day of the test, after exposure of the homosalate standard, MED's and static determination, another area measuring 5 cm×10 cm is designated. The test formulation is spread uniformly over the area at a concentration of 2.0 mg/cm² and allowed a fifteen minute drying period as before. Another adjacent site is selected for determination of a waterproof sunscreen standard. The standard has a known waterproof sun protection factor bracketing the expected sun protection factor of the test formulation. The following immersion schedule is employed:

20 minutes of moderate activity in water.
20 minutes rest period out of the water.
20 minutes of moderate activity in water.
20 minutes rest period out of the water.
20 minutes of moderate activity in water.
20 minutes rest period out of the water.
20 minutes of moderate activity in water.

Immersion is achieved indoors in a circulating whirlpool tub having a 1 h.p. pump operating at 3450 RPM delivering 8 g.p.m. through 8–1.5 cm diameter ports. The water is maintained at an average temperature of 75–80° F. The test area was air dried prior to exposure from the solar simulator. A second series of exposures on the test formulation is administered to the protected area, again using 25% increments. The exact series of exposures employed is determined by the controlled MED and the expected SPF of the product as defined above.

Sixteen to twenty four hours post exposure, the subjects are evaluated for delayed erythemic response. The smallest exposure or least amount of energy required to produce erythema (MED) in the treated site is recorded. SPF is then calculated according to the following equation:

$$SPF = \frac{MED \text{ Protected Skin}}{MED \text{ Unprotected Skin}}$$

EXAMPLE 1

The following sunscreen formulations are prepared essentially as described above.

| Component | Formulation No. 1[1] | 2 |
|---|---|---|
| Stearic acid | 3.0 | — |
| Triethanolamine | 1.5 | — |
| Carbopol 934[2] | 0.2 | — |
| Stearyl amido benzoate, sodium salt | — | 2.0 |
| Glycerol mono stearate | 1.0 | 1.0 |

-continued

| Component | Formulation No. 1[1] | 2 |
|---|---|---|
| Elefac I-205[3] | 8.0 | 8.0 |
| Ethylhexyl-p-methoxy cinnamate | 5.0 | 5.0 |
| 2-Phenyl-benzimidazole-5-sulfonic acid | 1.0 | 1.0 |
| TioSperse I[4] (% active TiO₂ in formulation) | 10.0 (4.0) | 10.0 (4.0) |
| Water | Q.S. to 100 | Q.S. to 100 |
| Stability[5] | stable | stable |
| pH | 7.55 | 7.6 |
| Sun Protection Factor (in vitro) | 15.5 | 23.8 |

[1]Comparative example.
[2]A homopolymer of acrylic acid crosslinked with an allyl ether of pentaerythritol or an allyl ether of sucrose, commercially available from BF Goodrich.
[3]Octyl dodecyl neopentanoate, commercially available from Bernel, Inc.
[4]A 40% by weight slurry of TiO₂ coated with aluminum stearate in Elefac I-205, commercially available from Collaborative Laboratories, Inc.
[5]Emulsion stability was evaluted via multiple criteria; specifically: 1) oven stability at 42° C. for 1 month, 2) comparison of emulsion micrographs obtained on day one vs. two weeks vs. one month, 3) measurement of conductivity and 4) rheological profile. Stable indicates that all criteria were satisfied.

EXAMPLE 2

The following sunscreen formulations are prepared essentially as described above.

Waterproof sunscreen formulations

| Component | Formulation No. 3[6] | 4 | 5 |
|---|---|---|---|
| Stearic acid | 3.0 | — | — |
| Triethanolamine | 1.5 | — | — |
| Carbopol 934 | 0.1 | — | — |
| Stearyl amido benzoate, sodium salt | — | 2.0 | 2.0 |
| Glycerol mono stearate | 1.0 | 1.0 | 1.0 |
| Elefac I-205 | 8.0 | 8.0 | 8.0 |
| Ethylhexyl-p-methoxy cinnamate | 3.5 | 3.5 | 3.5 |
| Benzophenone-3 | 1.5 | 1.5 | 1.5 |
| Tiosperse I (% active TiO₂ in formulation) | 10.0 (4.0) | 10.0 (4.0) | 10.0 (4.0) |
| Ganex V-220[7] | | | 0.5 |
| water | Q.S. to 100 | Q.S. to 100 | Q.S. to 100 |
| stability | stable | stable | stable |
| pH | 7.6 | 7.65 | 7.6 |
| sun protection factor (in vitro) | 14 | 22.1 | 22 |
| Waterproof sun protection factor (in vivo) | 15.3 | 21.8 | 22.7 |

[6]Comparative example.
[7]A polymer of vinylpyrrolidone and eicosene monomers, commercially available from GAF.

EXAMPLE 3

The following sunscreen formulations are prepared essentially as described above.

| | The following sunscreen formulations are prepared essentially as described above. | |
|---|---|---|
| | | Formulation No. |
| Component | 6[8] | 7 |
| Stearic acid | 3.0 | — |
| Triethanolamine | 1.5 | — |
| Carbopol 934[9] | 0.2 | — |
| Stearyl amido benzoate, sodium salt | | 2.0 |
| glycerol mono stearate | 1.0 | 1.0 |
| Elefac I-205 | 10.0 | 10.0 |
| ethylhexyl-p-methoxy cinnamate | 7.5 | 7.5 |
| Benzophenone-3 | 3.0 | 3.0 |
| 2-Phenyl-benzimidazole-5-sulfonic acid | 1.0 | 1.0 |
| Water | Q.S. | Q.S. |
| stability | stable | stable |
| pH | 7.65 | 7.6 |
| sun protection factor (in vitro) | 28.7 | 34.2 |

[8]Comparative example.
[9]A homopolymer of acrylic acid crosslinked with an allyl ether of pentaerythritol or an allyl ether of sucrose, commercially available from Goodrich.

EXAMPLE 4

Formulations 8–10 are prepared essentially as follows:

Water and stearyl amido benzoate, sodium salt, are combined at room temperature and heated with mixing to about 75–80° C. An oil phase is prepared by combining the oil phase components and mixing with heating to about 77–82° C. When preparing compositions containing titanium dioxide, a slurry of titanium dioxide is added to a mixture of completely solubilized oil phase components at a temperature of about 55–60° C.; the mixture is then heated to about 75–80° C. and homogenized. Subsequently, the oil phase is added to the water phase with constant mixing. The resulting mixture is mixed at 75° C. for about 30 minutes and then allowed to cool with continuous mixing to about at least 30° C. At a temperature below 50° C., a preservative is optionally added and the pH is optionally adjusted with, for example, citric acid.

| | Formulation No. | | | | |
|---|---|---|---|---|---|
| Components | 4[10] | 8 | 5[10] | 9 | 10 |
| Stearyl amido benzoate, sodium salt | 2 | 2 | 2 | 2 | 2 |
| Glycerol mono stearate | 1 | 1 | 1 | 1 | 1 |
| Elefac I-205 | 8 | 8 | 8 | 8 | 8 |
| Ethyl hexyl p-methoxy cinnamate | 3.5 | 3.5 | 3.5 | 3.5 | 3.5 |
| Benzophenone-3 | 1.5 | 1.5 | 1.5 | 1.5 | 1.5 |
| TioSperse I (% active TiO$_2$ in formulation) | 10 (4) | 10 (4) | 10 (4) | 10 (4) | 10 |
| Cetyl alcohol | | 1 | | | 1 |
| Ganex V-220 | | | 0.5 | | |
| Xantham Gum | | | | 0.1 | 0.2 |
| Magnesium Aluminum Silicate | | | | 0.3 | 0.5 |
| Water | Q.S. to 100% | Q.S. to 100% | Q.S. to 100% | Q.S. to 100% | Q.S. to 100% |
| SPF (in vitro) | 22.1 | 19.1 | 22.0 | — | 25.2 |

[10]From Example 2.

What is claimed is:

1. A method for increasing the sun protection factor of an oil and water sunscreen emulsion comprising adding a phthalic acid derivative to an oil and water emulsion containing at least one sunscreening agent in an amount effective to increase the sun protection factor of the emulsion, the phthalic acid derivative having the formula:

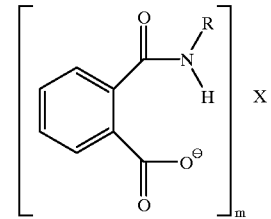

where
R represents $C_8$–$C_{40}$ alkyl, $C_8$–$C_{40}$ alkenyl, alkylaryl where the alkyl portion is $C_8$–$C_{40}$ alkyl, aryl, $C_3$–$C_7$ cycloalkyl, or $R_1$—O—$R_2$ where $R_1$ and $R_2$ independently represent $C_1$–$C_{22}$ alkyl, $C_1$–$C_{22}$ alkenyl, alkylaryl where the alkyl portion is $C_1$–$C_{22}$ alkyl, aryl, or $C_3$–$C_7$ cycloalkyl;
X represents a cation; and
m is an integer satisfying the valency of X.

2. A method according to claim 1, wherein the amount of phthalic acid derivative is about 0.1 to 15% by weight of the emulsion.

3. A method according to claim 2, wherein the phthalic acid derivative is added to the emulsion with a low hydrophilic/lipophilic balance emulsifier.

4. A method according to claim 3, wherein the amount of phthalic acid derivative is about 1% to 5% by weight of the emulsion.

5. A method according to claim 4, wherein the amount of oil in the emulsion is from about 1 to 65% by weight of the emulsion.

6. A method according to claim 5, wherein the emulsion comprises at least one sunscreen compound and the oil comprises at least one hydrophobic oil.

7. A method according to claim 6, wherein the sunscreen compound is an organic sunscreen agent that absorbs UV-A or UV-B radiation, or UV-A and UV-B radiation.

8. A method according to claim 7, further comprising at least one inorganic sunscreen agent capable of scattering, reflecting or absorbong UV radiation.

9. A method according to claim 8, wherein the emulsion is an oil-in-water emulsion.

10. A sunscreen composition comprising an emulsion of an oil, water, a sunscreen compound, and a sun protection factor enhancement system, the sun protection factor enhancement system comprising a phthalic acid derivative in an amount effective to enhance the sun protection factor of the emulsion, the phthalic acid derivative having the formula:

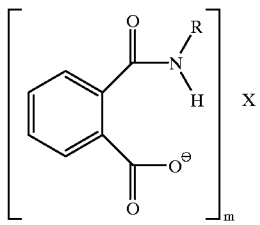

where represents $C_8$–$C_{40}$ alkyl, $C_8$–$C_{40}$ alkenyl, alkylaryl where the alkyl portion is $C_8$–$C_{40}$ alkyl, aryl, $C_3$–$C_7$ cycloalkyl, or $R_1$—O—$R_2$ where $R_1$ and $R_2$ independently represent $C_1$–$C_{22}$ alkyl, $C_1$–$C_{22}$ alkenyl, alkylaryl where the alkyl portion is $C_1$–$C_{22}$ alkyl, aryl, or $C_3$–$C_7$ cycloalkyl;

X represents a cation; and m is an integer satisfying the valency of X.

11. A composition according to claim 10, wherein the amount of the phthalic acid derivative is about 0.1 to 15% by weight of the emulsion.

12. A composition according to claim 11, wherein the sun protection enhancement system further comprises a low hydrophilic/lipophilic balance emulsifier.

13. A composition according to claim 12, wherein the amount of the phthalic acid derivative is about 1% to 5% by weight of the emulsion.

14. A composition according to claim 13, wherein the amount of oil in the emulsion is from about 1 to 65% by weight of the emulsion.

15. A composition according to claim 14, wherein the oil phase comprises at least one oil.

16. A composition according to claim 15, wherein the sunscreen compound absorbs UVA and UVB radiation or UVA or UVB radiation.

17. A composition according to claim 16, further comprising at least one inorganic sunscreen capable of scattering, reflecting and absorbing UV radiation.

18. A composition according to claim 17, wherein the emulsion is an oil-in-water emulsion.

19. A method according to claim 1, wherein he sunscreen agent is an inorganic sunscreen, an organic sunscreen, or a combination thereof.

20. A composition according to claim 10, wherein the sunscreen compound is an organic sunscreen, an inorganic sunscreen or a mixture thereof.

* * * * *

UNITED STATES PATENT AND TRADEMARK OFFICE
CERTIFICATE OF CORRECTION

PATENT NO.  : 6,165,449
DATED       : December 26, 2000
INVENTOR(S) : Lillian George et al.

It is certified that error appears in the above-identified patent and that said Letters Patent is hereby corrected as shown below:

Column 11,
Line 17, delete "represents" and insert -- R represents --.

Signed and Sealed this

Nineteenth Day of August, 2003

JAMES E. ROGAN
*Director of the United States Patent and Trademark Office*